United States Patent
Ginn et al.

(10) Patent No.: US 6,846,319 B2
(45) Date of Patent: Jan. 25, 2005

(54) DEVICES FOR SEALING OPENINGS THROUGH TISSUE AND APPARATUS AND METHODS FOR DELIVERING THEM

(75) Inventors: Richard S. Ginn, San Jose, CA (US); Stephen M. Salmon, Sunnyvale, CA (US); Ronald J. Jabba, Redwood City, CA (US)

(73) Assignee: Core Medical, Inc., Sunnyvale, CA (US)

( * ) Notice: Subject to any disclaimer, the term of this patent is extended or adjusted under 35 U.S.C. 154(b) by 344 days.

(21) Appl. No.: 09/738,431

(22) Filed: Dec. 14, 2000

(65) Prior Publication Data

US 2002/0077656 A1 Jun. 20, 2002

(51) Int. Cl.[7] .............................................. A61B 17/08
(52) U.S. Cl. ..................... 606/213; 604/8; 623/11.11
(58) Field of Search ............................. 606/213, 192, 606/191, 194, 195, 1, 65, 72, 73; 600/32; 623/11.11, 1.11; 604/8

(56) References Cited

U.S. PATENT DOCUMENTS

| | | |
|---|---|---|
| 287,046 A | 10/1883 | Norton |
| 3,015,403 A | 1/1962 | Fuller |
| 3,944,114 A | 3/1976 | Coppens |
| 4,525,157 A | 6/1985 | Vaillancourt |
| 4,738,658 A | 4/1988 | Magro et al. |
| 4,744,364 A | 5/1988 | Kensey |
| 4,852,568 A | 8/1989 | Kensey |
| 4,878,915 A | 11/1989 | Brantigan |
| 5,015,247 A | 5/1991 | Michelson |
| 5,021,059 A | 6/1991 | Kensey et al. |
| 5,032,125 A | 7/1991 | Durham et al. |
| 5,061,274 A | 10/1991 | Kensey |
| 5,114,032 A | 5/1992 | Laidlaw |
| 5,192,301 A | 3/1993 | Kamiya et al. |
| 5,192,302 A | 3/1993 | Kensey et al. |
| 5,222,974 A | 6/1993 | Kensey et al. |
| 5,275,616 A | 1/1994 | Fowler |
| 5,290,310 A | 3/1994 | Makower et al. |
| 5,292,332 A | 3/1994 | Lee |
| 5,306,254 A | 4/1994 | Nash et al. |
| 5,320,639 A | 6/1994 | Rudnick |
| 5,334,216 A | 8/1994 | Vidal et al. |
| RE34,866 E | 2/1995 | Kensey et al. |
| 5,411,520 A | 5/1995 | Nash et al. |
| 5,425,757 A | 6/1995 | Tiefenbrun et al. |
| 5,443,481 A | 8/1995 | Lee |
| 5,486,195 A | 1/1996 | Myers et al. |
| 5,492,763 A * | 2/1996 | Barry et al. ............. 604/264 |
| 5,522,840 A | 6/1996 | Krajicek |
| 5,571,181 A | 11/1996 | Li |
| 5,645,565 A | 7/1997 | Rudd et al. |
| 5,690,674 A | 11/1997 | Diaz |
| 5,728,116 A * | 3/1998 | Rosenman ............. 606/151 |

(List continued on next page.)

OTHER PUBLICATIONS

PCT Publication No. WO 00/71032 A2, "Hemostatic Device for Angioplasty", Marius Saines, Nov. 30, 2000.

*Primary Examiner*—Peter Nerbun
(74) *Attorney, Agent, or Firm*—Orrick, Herrington & Sutcliffe LLP; James W. Geriak

(57) ABSTRACT

An apparatus for sealing a passage through tissue includes an elongate shaft and a cylindrical plug disposed on a distal end of the shaft, the plug including a helical thread on its outer surface. Intestinal submucosa may be secured to the plug, e.g., in a cavity in its distal end, that may be delivered into the passage. Alternatively, the plug may be formed from a bioabsorbable material and may be released from the shaft within the passage. The plug is threaded into the passage, thereby engaging the tissue to seal the passage. The shaft is rotated until it engages a blood vessel within the tissue while monitoring blood flow through the vessel. The shaft is rotated to thread the plug into the passage until blood flow ceases through the vessel, whereupon rotation of the shaft is reversed to back the plug until blood flow through the vessel resumes.

20 Claims, 3 Drawing Sheets

U.S. PATENT DOCUMENTS

| | | | |
|---|---|---|---|
| 5,728,122 A | | 3/1998 | Leschinsky et al. |
| 5,871,474 A | | 2/1999 | Hermann et al. |
| 5,871,501 A | | 2/1999 | Leschinsky et al. |
| 5,871,525 A | | 2/1999 | Edwards et al. |
| 5,989,230 A | * | 11/1999 | Frassica .................. 604/510 X |
| 6,016,806 A | | 1/2000 | Webb |
| 6,082,362 A | * | 7/2000 | Webb ........................ 604/8 X |
| 6,126,675 A | * | 10/2000 | Shchervinsky et al. ..... 606/213 |
| 6,296,657 B1 | * | 10/2001 | Brucker ....................... 606/213 |
| 6,306,114 B1 | * | 10/2001 | Freeman et al. ............ 604/8 X |
| 6,447,539 B1 | * | 9/2002 | Nelson et al. ............. 623/1.11 |

* cited by examiner

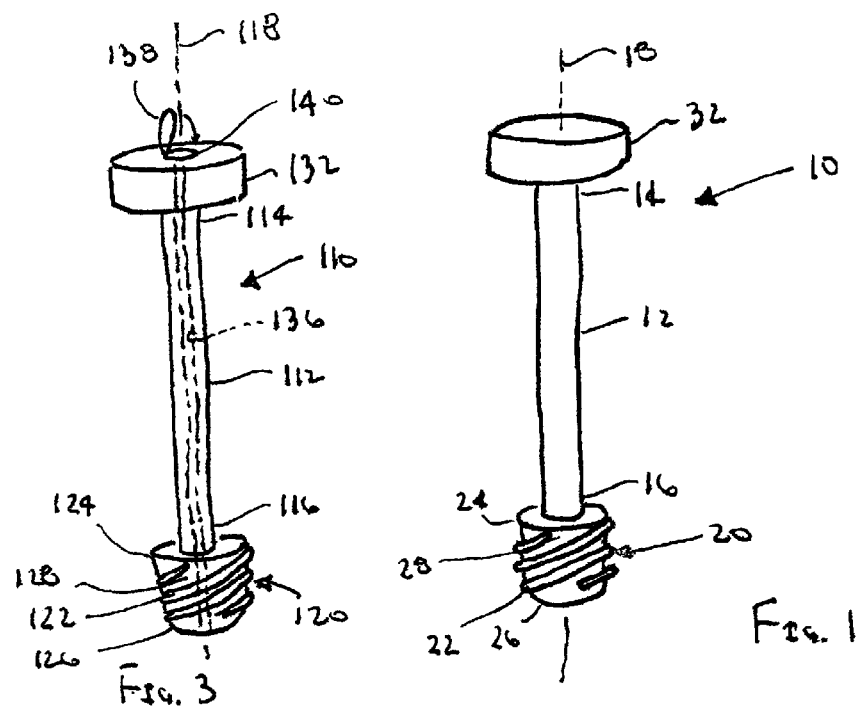
Fig. 3
Fig. 1
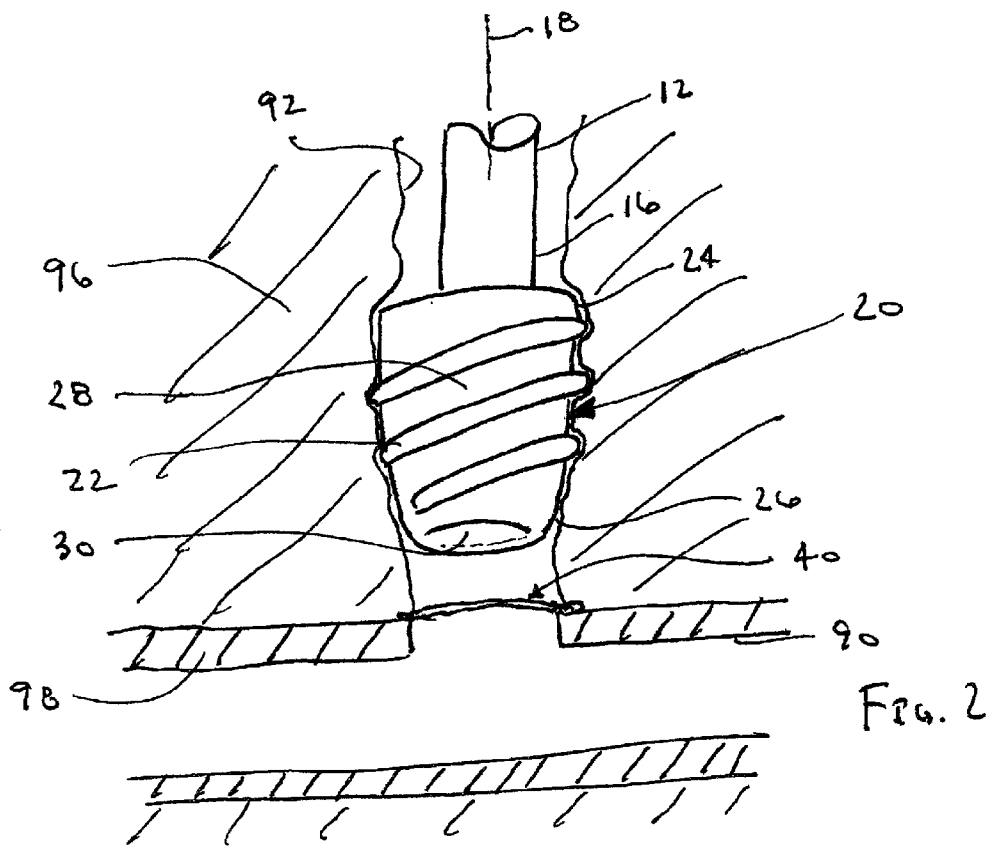
Fig. 2

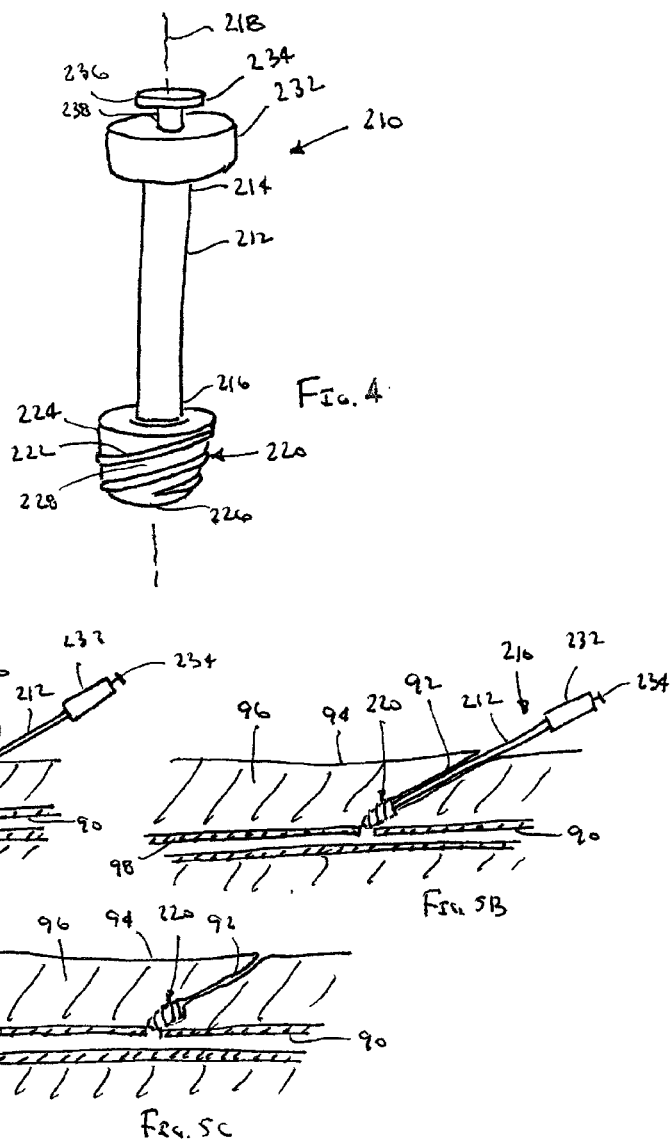

DEVICES FOR SEALING OPENINGS THROUGH TISSUE AND APPARATUS AND METHODS FOR DELIVERING THEM

FIELD OF THE INVENTION

The present invention relates generally to systems and methods for sealing or closing passages through tissue, and more particularly to devices for sealing punctures or other openings communicating with body lumens, such as blood vessels, and to apparatus and methods for delivering such devices.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

Accordingly, devices for sealing punctures or other passages through tissue, e.g., an opening into a blood vessel, would be considered useful.

SUMMARY OF THE INVENTION

The present invention is directed to systems and methods for sealing or closing passages through tissue, such as punctures communicating with blood vessels or other body lumens.

In accordance with one aspect of the present invention, an apparatus for sealing a passage through tissue is provided that includes an elongate member having a proximal end and a distal end, and a generally cylindrical plug member disposed on the distal end of the elongate member, the plug member including an outer surface having a helical thread thereon.

In one embodiment, the plug member includes a cavity in its distal end. A hemostasis-promoting material, such as intestinal submucosa, or an infection-resistant material, may be disposed in the cavity or otherwise secured to the plug member. The material may be delivered into the passage to facilitate hemostasis and/or healing of tissue proximate the passage. Alternatively, a lumen may be provided that extends from the proximal end of the elongate member through the plug member, and a seal may be provided for selectively sealing the lumen. The lumen may facilitate insertion of the apparatus and/or may facilitate monitoring hemostasis within the tissue.

In another embodiment, the plug member is releasable from the elongate member. Preferably, the plug member is formed from a bioabsorbable material such that the plug member may be released within the tissue to seal the passage, and allowed to be absorbed by the tissue over time. The elongate member preferably includes an actuator for releasing the plug member from the distal end of the elongate member. Preferably, cooperating connectors are provided on the distal end of the elongate member and the plug member for releasably securing the plug member to the distal end of the elongate member. Alternatively, the elongate member may include an expandable member, such as a frame, on its distal end that may be selectively expanded to engage an interior wall of the plug member and collapsed to release the plug member.

In accordance with another aspect of the present invention, a method is provided for sealing a passage through tissue. An apparatus is provided that includes an elongate member and a generally cylindrical plug member disposed on a distal end of the elongate member, the plug member including an outer surface having a helical thread thereon.

The plug member is inserted into the passage, and the elongate member is rotated, thereby threading the plug member within the passage, the plug member engaging the tissue to substantially seal the passage. In one preferred method, the passage communicates with a blood vessel within the tissue, and the elongate member is rotated until the plug member substantially seals a wall of the blood vessel. The plug member may be left within the passage for sufficient time for hemostasis to occur, whereupon the plug member may be removed from the passage. In addition or alternatively, a hemostasis-promoting material may be provided within a cavity in a distal end of the plug member, and the material may be left in the passage when the plug member is removed. In a further alternative, the plug member itself may be released from the elongate member within the passage. Preferably, in this embodiment, the plug member is formed from a bioabsorbable material.

In another preferred embodiment, the elongate member is rotated until it engages a blood vessel within the tissue. Blood flow at a location downstream of the blood vessel may be monitored, e.g., by feeling the patient's pulse. The elongate member may be rotated in a first direction to thread the plug member deeper into the passage until blood flow substantially ceases downstream of the blood vessel. Rotation of the elongate member may then be reversed to back the plug member a predetermined distance, thereby allowing blood flow to resume downstream of the blood vessel. The plug member may be released at this location or otherwise maintained at this location until hemostasis and/or healing occurs.

Other objects and features of the present invention will become apparent from consideration of the following description taken in conjunction with the accompanying drawings.

BRIEF DESCRIPTION OF THE DRAWINGS

FIG. 1 is a perspective view of a preferred embodiment of an apparatus for sealing a passage through tissue, in accordance with the present invention.

FIG. 2 is a cross-sectional side view showing a plug member on the apparatus of FIG. 1 being used to deliver a patch to seal an opening in a wall of a blood vessel.

FIG. 3 is a perspective view of an alternative embodiment of an apparatus for sealing a passage through tissue, in accordance with the present invention.

FIG. 4 is a perspective view of a preferred embodiment of a detachable plug and delivery apparatus, in accordance with the present invention.

FIGS. 5A–5C are cross-sectional views of the apparatus of FIG. 4 being used to deliver the plug into a passage communicating with a blood vessel.

DETAILED DESCRIPTION OF THE PREFERRED EMBODIMENTS

Figure 6B:
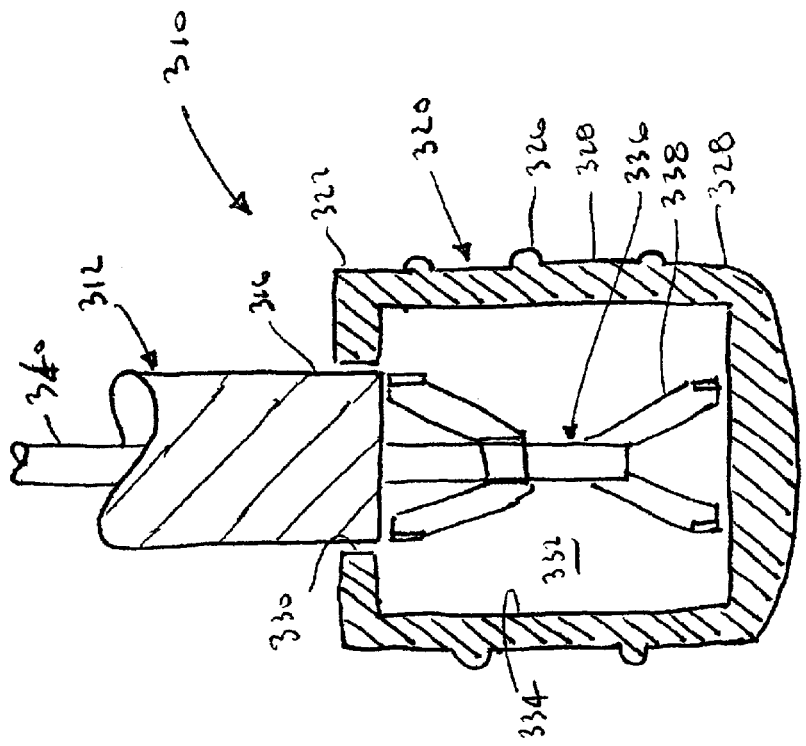
FIGS. 6A and 6B are cross-sectional views of another detachable plug and a delivery apparatus including an expandable frame shown in expanded and collapsed states, respectively, for securing and releasing the plug member.

Turning now to the drawings, FIG. 1 shows a first preferred embodiment of an apparatus 10 for sealing a passage through tissue, in accordance with the present invention. Generally, the apparatus 10 includes an elongate shaft 12 and a plug member 20. The shaft 12 has a proximal end 14 and a distal end 16 defining a longitudinal axis 18 therebetween. A handle 32 may be provided on the proximal end 14 of the shaft 12 for facilitating manipulation of the apparatus 10, e.g., to facilitate rotation of the apparatus 10 into a passage, as described below.

The plug member 20 is disposed on the distal end 16 of the shaft 12 and includes a helical thread 22 extending at least partially between its proximal and distal ends 24, 26. The plug member 20 is a substantially rigid body having a generally cylindrical shape and defining an outer surface 28 along which the helical thread 22 extends. The helical thread 22 preferably is substantially rigid and has a substantially square cross-section to facilitate sealing of a passage into which the plug member 20 is threaded. Alternatively, the plug member 20 may be a semi-rigid or flexible body or may have a substantially flexible distal tip (not shown), e.g., to facilitate atraumatic insertion of the plug member 20 into the passage.

Preferably, the shaft 12 has a cross-section that is substantially smaller than a cross-section of the plug member 20, e.g., to minimize dilation of a passage into which the apparatus 10 is inserted. The plug member 20 may be tapered between the proximal and distal ends 24, 26 and/or the distal end 26, or only partially tapered, e.g., at the distal end 26. In addition or alternatively, the distal end 26 may be rounded to facilitate advancement of the plug member 20 into a passage through tissue.

In a preferred embodiment, the helical thread 22 is integrally formed on the outer surface 28 of the plug member 20. For example, the plug member 20 and thread 22 may be formed by injection molding. Alternatively, the threads may be cut or otherwise formed in the outer surface 28 of the plug member 20. The plug member 20 may be formed from a biocompatible material, preferably a plastic, such as polyethylene or polyester. The plug member 20 may be substantially permanently attached to the distal end 16 of the shaft 12, for example, by mechanical detents and/or an adhesive. Alternatively, the shaft 12 and plug member 20 may also be integrally formed as a single piece. In a further alternative, the plug member 20 may releasably attached to the shaft 12, as described below.

In one embodiment, the plug member 20 includes a cavity, such as concave recess 30, in its distal end 26. A material (not shown) may be provided in the cavity 30, such as intestinal submucosa, collagen, an infection-resistant material, and the like. Such material may promote hemostasis and/or healing of the tissue, as will be appreciated by those skilled in the art. Alternatively, the material may be otherwise detachably secured to the distal end 26 of the plug member 20, either within the cavity 30 or across the distal end 26 without a cavity (not shown). For example, the material may be secured using a biodegradable adhesive or a mechanical fastener, such as one or more clips (not shown). Such a fastener may be actuated from the proximal end 14 of the shaft 12 to release the material, or the material may otherwise be automatically released upon withdrawal of the plug member 20.

Turning to FIG. 2, during use, the plug member 20 may be used to seal and/or close a passage through tissue 96, such as a puncture 92 communicating with a blood vessel 90 or other body lumen. The puncture 92 may be used to provide percutaneous access to the blood vessel 90. For example, the puncture 92 may facilitate performing an endovascular procedure within a patient's vasculature, such as angioplasty, stenting, atherectomy, and the like, or may otherwise provide access via the blood vessel 90 to a region within the patient's body. Upon completion of the procedure, any instruments, such as an introducer sheath (not shown), may be removed from the blood vessel 90 and puncture 92.

The apparatus 10 may then be introduced into the puncture 92, for example, by at least partially inserting the plug member 20 into the puncture 92. Preferably, the outer surface 28 and threads 22 engage tissue 96 surrounding the puncture 92, thereby substantially sealing the puncture 92 from fluids, such as blood, within the vessel 90. The apparatus 10 may then be rotated in a first direction about its longitudinal axis 18 to thread the plug member 20 substantially atraumatically deeper into the puncture 92. Preferably, the plug member 20 is advanced until its distal end 26 is proximate to the wall 98 of the vessel 90.

In the embodiment shown in FIG. 2, a patch 40, e.g., of intestinal submucosa or other hemostasis-promoting material, is provided in a cavity 30 within the distal end 26 of the plug member 20. For example, U.S. Pat. No. 2,167,251, issued to Rogers, discloses exemplary materials that may be included in the cavity 30 or otherwise detachably secured to the plug member 20. The disclosure of this reference and any others cited therein are expressly incorporated herein by reference.

When the plug member 20 is advanced proximate the wall 98 of the vessel 90, the patch 40 is delivered within or adjacent to the wall 98. The patch 40 may promote hemostasis and/or healing of the wall 98 at the puncture site. After hemostasis and/or a desired level of healing has occurred, the plug member 20 may be withdrawn from the puncture 92 by rotating the apparatus 10 in a second direction opposite the first direction. Alternatively, the patch 40 may be delivered to the wall 98 at the puncture site simply by releasably securing the patch 40 to the distal end 26 of the plug member 20, as described above. Alternatively, the plug member 20 may be advanced into the puncture 92 without a patch to seal the puncture and allow hemostasis and/or healing to occur naturally before removal of the plug member 20.

Turning to FIG. 3, another embodiment of an apparatus 110 is shown for sealing a passage through tissue. Similar to the previous embodiment, the apparatus 110 includes an elongate shaft 112, a plug member 120 disposed on a distal end 116 of the shaft 112, and a handle 132 on a proximal end 114 of the shaft 112. In addition, the apparatus 110 includes a lumen 136 extending from the proximal end 114 of the shaft 112 distally through the plug member 120. A seal 138, such as a hinged cap, may be provided for sealing an opening 140 communicating with the lumen 138. The seal 138 and opening 140 may be provided on the handle 132 or elsewhere on the proximal end 114 of the shaft 112.

Use of the apparatus 110 is similar to the previous embodiment, i.e., the plug member 120 is threaded into a puncture, e.g., to seal an opening in a wall of a blood vessel (not shown). The seal 138 is initially provided closed, thereby preventing blood or other fluid from passing through the lumen 136 to the proximal end 114 of the shaft 112. Alternatively, the cap 138 may be initially provided open, such that when the distal end 126 of the plug member 120 starts to enter a blood vessel, blood within the vessel may enter and pass proximally through the lumen and exit the opening 140, thereby providing a visual indicator that the plug member 120 has reached the vessel. The seal 138 may then be sealed to prevent further flow of fluid therethrough.

Periodically, the seal 138 may be opened to see if fluid flows from within the vessel through the lumen 136. Once hemostasis occurs, such flow may no longer occur when the seal 138 is opened, thereby indicating that the apparatus 110 may be removed. Alternatively, the lumen 136 may be coupled to another tube or other external system that may facilitate monitoring of fluid flow through the lumen 136.

Turning to FIG. 4, another preferred embodiment of an apparatus 210 is shown for sealing a passage through tissue. Similar to the previous embodiments, the apparatus 210 includes an elongate shaft 212, a plug member 220 disposed on a distal end 216 of the shaft 212, and a handle 232 on a proximal end 214 of the shaft 212. Unlike the previous embodiment, however, the plug member 220 is releasable from the shaft 212. The plug member 220 preferably is at least partially formed from bioabsorbable material, such as collagen, PGA's, PLA's, and the like, that may be at least partially absorbed by the patient's body over time.

The plug member 220 and the distal end 216 of the shaft 212 generally include cooperating connectors (not shown) for releasably securing the plug member 220 to the shaft 212. For example, the plug member 220 may include a recess (not shown) in its proximal end 224 and the shaft 212 may include a mechanism, e.g., radially projecting fingers, for frictionally engaging the wall of the recess. Alternatively, the recess may include slots for positively receiving the mechanism on the shaft 212. In a further alternative, the plug member 220 may include a hub (not shown) extending from its proximal end 224 and the shaft 212 may include a mechanism for detachable securing the hub to the shaft 212.

Preferably, the handle 232 includes an actuator 234 that may be activated to release the connectors securing the plug member 220 to the shaft 212. For example, the actuator 234 may include a button 236 coupled to a control rod or wire 238 that extends through the shaft 212 to its distal end 216. Upon depression of the button 236, the control rod 238 may be moved, thereby disengaging the connector on the shaft 212 from the mating connector on the plug member 220. In another alternative, the distal end 216 of the shaft 212 and the plug member 220 may include mating threads (not shown) so that the shaft 212 may be rotated with respect to the plug member 220 to release the plug member 220. In this embodiment, the mating threads should wind helically in the same direction as the helical threads 224 to ensure that the plug member 220 is not released prematurely from the shaft 212.

Turning to FIGS. 5A–5C, the apparatus 210 may be used to seal a passage 92 extending from a patient's skin 94 through tissue 96 to a blood vessel 90 or other body lumen. The passage 92 may be formed, a procedure performed within the patient's body via the vessel 90, and any instruments removed from the passage 92. The plug member 220 may be introduced into the passage 92, and the apparatus 210 may be rotated to thread the plug member 220 into the passage 92. Preferably, the threads 222 facilitate controlled advancement of the plug member 220 through the tissue 94 and/or facilitate substantially sealing of fluid flow through the passage 92.

Preferably, while advancing the plug member 220, blood flow at a location downstream of the blood vessel 90 is monitored. For example, the patient's pulse may be manually or automatically monitored downstream of the puncture site. The apparatus 210 may be rotated, advancing the plug member 220 until blood flow substantially ceases downstream of the blood vessel. This may indicate that the plug member 220 has engaged and compressed the blood vessel 90, as shown in FIG. 5A.

Rotation of the apparatus 210 may then be reversed to back the plug member 220 a predetermined distance, thereby allowing blood flow to resume downstream of the blood vessel 90. For example, the threads 222 may have a predetermined thread spacing such that the apparatus 210 may be rotated a predetermined number of times to accurately withdraw the plug member 220 from compressing the blood vessel 90 while still substantially sealing the passage 92 at the wall 98 of the vessel 90, as shown in FIG. 5B.

The plug member 220 may then be released from the shaft 212, e.g., by depressing the actuator 234, and the shaft 212 withdrawn from the passage 92, leaving the plug member 220 within the passage 92, as shown in FIG. 5C. Because the plug member 220 is bioabsorbable, the plug member 220 may be absorbed by the tissue over time, thereby allowing the wall 98 of the vessel 90 and tissue 96 surrounding the passage 92 to at least partially heal before the plug member 220 is absorbed.

In an alternative embodiment, the plug member 220 may be biocompatible, but not bioabsorbable. In this alternative, it may be desirable or necessary to subsequently remove the plug member 220, e.g., once hemostasis and/or healing of the wall 98 of the vessel 90 has occurred. The plug member 220 may be retrieved by creating an incision in the patient's skin 94 and/or through the tissue 96 (e.g., if the passage has healed), and introducing an apparatus (not shown) to retrieve the plug member 220, such as a shaft having a connector on its end, similar to the apparatus 210 used to deliver the plug member 220.

Figure 6A:
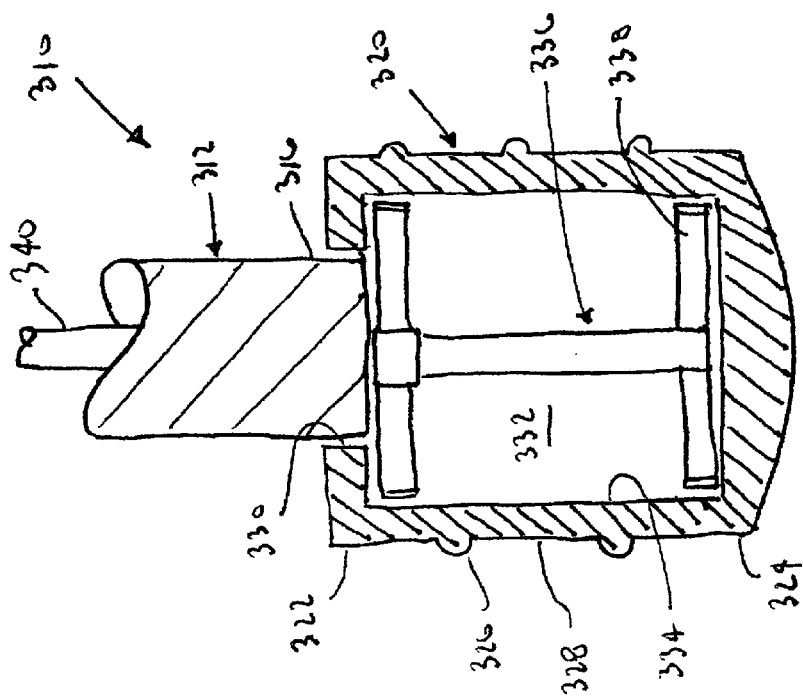

Turning to FIGS. 6A and 6B, yet another preferred embodiment of an apparatus 310 is shown for sealing a passage through tissue. Similar to the previous embodiments, the apparatus 310 includes an elongate shaft 312, a plug member 320 disposed on a distal end 316 of the shaft 312, and a handle (not shown) on a proximal end (also not shown) of the shaft 312.

The plug member 320 is preferably at least partially formed from bioabsorbable material that may be absorbed by the patient's body over time, similar to the embodiment described previously. The plug member 320 includes proximal and distal ends 322, 324 and a helical thread 326 extending along an exterior surface 328 thereof. In addition, an opening 330 in the proximal end 322 communicates with an interior cavity 332 defined by an interior wall 334.

An expandable member 336 extends from the distal end 316 of the shaft 312 for securing the plug member 320 to the shaft 312 during delivery. In a preferred embodiment, the expandable member 336 is a mechanically expandable frame including a plurality of radially movable arms 338. Preferably, the handle on the shaft 312 includes an actuator (not shown) that may be activated to control an actuator rod or wire 340, to selectively collapse and/or expand the frame 336 to release or secure the plug member 320 to the shaft 312, respectively.

The frame 336 may be collapsed and inserted through the opening 330 into the interior cavity 332 of the plug member 320. The frame 336 may then be expanded to an expanded state, shown in FIG. 6A, to engage the interior wall 334 of the plug member 320, thereby substantially securing the plug member 320 to the distal end 316 of the shaft 312. Subsequently, the frame 336 may be selectively collapsed to a collapsed state, shown in FIG. 6B, for releasing the plug member 320 from the shaft 312. In the collapsed state, the frame 336 may provided a relatively low cross-section or profile, thereby facilitating removal of the shaft 312 from a passage within which the plug member 320 is delivered.

In the expanded state, the radial arms 338 of the frame 336 may engage the interior wall 334 of the plug member 320 at a plurality of discrete locations. In this form, the plug member 320 is preferably sufficiently rigid that it is self-supporting when the frame 336 is collapsed. Alternatively, the radial arms 332 may support elongate bands (not shown), e.g., that extend between respective arms 322 that may provide greater surface contact with the interior wall 334 of the plug member 320. These bands may extend circumferentially and/or axially between arms 338 of the frame 336. Thus, the frame 336 may provide structural support for the plug member 320, e.g., during advancement of the apparatus 310 into a passage through tissue (not shown).

In an alternative embodiment, the expandable member may be an inflatable member (not shown), such as an elastic or inelastic balloon. Preferably, the balloon is substantially inelastic such that, when the balloon is fully expanded, it has a shape similar to the shape of the interior cavity 332 within the plug member 320. The balloon may engage the interior wall 334 of the plug member 320 to substantially support the plug member 320 during delivery. The balloon may be selectively inflated or deflated to secure the plug member 320 on the shaft 312 or to release the plug member 320 from the shaft 312, respectively.

The plug member 320 may be delivered to seal a passage through tissue, for example, using the method described above. The expandable member 330 (whether mechanical or inflatable) may be expanded to secure the plug member 320 on the shaft 312. The plug member 320 may be introduced into a passage, and the apparatus 310 may be rotated to thread the plug member 320 into the passage. Once advanced to a desired location, the plug member 320 may be released from the shaft 312, e.g., by collapsing the expandable member 330. The shaft 312 may then be withdrawn from the passage, leaving the plug member 320 within the passage.

An apparatus in accordance with the present invention may be used for procedures other than a surgical procedure. For example, an apparatus in accordance with the present invention may be used to seal temporarily or indefinitely other passages, such as wounds, punctures, and the like that extend through tissue. The apparatus may be used in an emergency setting, e.g., to seal a bullet wound or other puncture temporarily until the patient may be subsequently treated and/or transported to a location where conventional surgery or other treatment may be performed.

The apparatus may be removably introduced into the passage to seal it and/or may be deployed within the passage. A bleed back lumen, such as that described above, may be used to position the apparatus. Alternatively, flow through a blood vessel or other body passage proximate the passage may be monitored to position the plug member relative to the vessel, similar to the method described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. In an apparatus for sealing a passage through tissue which communicates with a body lumen, the improvement comprising:

an elongate shaft having a proximal end and a distal end;
an opening in the proximal region of the elongate shaft,
a plug member disposed on the distal end of the elongate shaft, the elongate shaft having a cross-section that is substantially smaller than a cross-section of the plug member, and
an opening in the distal region of said plug, wherein said plug member and said elongate shaft have a position indicating lumen therein which extends from the opening in the distal region of said plug to the opening in the proximal region-of said elongate shaft.

2. The apparatus of claim 1, wherein the plug member is at least partially tapered at its distal end.

3. The apparatus of claim 1, further comprising at least one of a hemostasis-promoting material and an infection-resistant material secured to a distal end of the plug member.

4. The apparatus of claim 1, wherein the plug member is releasable from the elongate shaft.

5. The apparatus of claim 4, wherein the elongate shaft comprises an actuator for releasing the plug member from the distal end of the elongate shaft.

6. The apparatus of claim 4, further comprising cooperating connectors on the distal end of the elongate shaft and on the plug member for releasably securing the plug member to the distal end of the elongate shall.

7. The apparatus of claim 4, wherein the plug member comprises bioabsorbable material.

8. The apparatus of claim 1, wherein the plug member is substantially permanently attached to the distal end of the elongate shaft.

9. The apparatus of claim 1, wherein the elongate shaft is provided with a seal for selectively sealing the lumen.

10. The apparatus of claim 9, wherein the seal is disposed on the proximal end of the elongate shaft.

11. In an apparatus for sealing a passage through tissue which communicates with a body lumen, the improvement comprising:

an elongate shaft having a proximal end and a distal end;

an opening in the proximal region of the elongate shaft, a plug member substantially permanently attached to the distal end of the elongate shaft, and an opening in the distal region of said plug, wherein said plug member and said elongate shaft have a position indicating lumen therein which extends from the opening in the distal region of said plug to the opening in the proximal region of the elongate shaft.

12. The apparatus of claim 11, wherein the plug member is at least partially tapered at its distal end.

13. The apparatus of claim 11, wherein the plug member comprises a cavity in its distal end.

14. The apparatus of claim 13, further comprising at least one of a hemostasis-promoting material and an infection-resistant material disposed in the cavity.

15. The apparatus of claim 14, wherein the material comprises intestinal submucosa.

16. The apparatus of claim 11, further comprising at least one of a hemostasis-promoting material and an infection-resistant material secured to a distal end of the plug member.

17. The apparatus of claim 11, wherein the plug member comprises bioabsorbable material.

18. The apparatus of claim 11, wherein the elongate shaft is provided with a seal for selectively sealing the lumen.

19. The apparatus of claim 18, wherein the seal is disposed on the proximal end of the elongate shaft.

20. In an apparatus for sealing a passage through tissue which communicates with a body lumen, the improvement comprising:

an elongate member having a proximal end and a distal end;

an opening in the proximal region of the elongate shaft, a plug member substantially permanently attached to the distal end of the elongate shaft, the plug member comprising a helical thread on its outer surface, the elongate member having a cross section that is substantially smaller than a cross section of the plug member, and an opening in the distal region of said plug wherein said plug member and said elongate shaft have a position indicating lumen therein which extends from the opening in the distal region of said plug to the opening in the proximal region of said elongate shaft.

\* \* \* \* \*